United States Patent

Kuroda et al.

Patent Number: 4,791,113
Date of Patent: Dec. 13, 1988

[54] MITOMYCIN DERIVATIVES AS ANTILEUKEMIA AGENTS

[75] Inventors: Tokuyuki Kuroda, Shizuoka; Koji Hisamura, Mie; Tohru Sugaya, Shizuoka; Yutaka Ohsawa, Shizuoka; Hideo Ueno, Shizuoka; Makoto Morimoto, Shizuoka; Tadashi Ashizawa, Shizuoka, all of Japan

[73] Assignee: Kyowa Hakko Kogyo Kabushiki Kaisha, Japan

[21] Appl. No.: 57,889

[22] Filed: May 12, 1987

[30] Foreign Application Priority Data

May 14, 1986 [JP] Japan .................. 61-110395
Nov. 26, 1986 [JP] Japan .................. 61-281585

[51] Int. Cl.$^4$ .............. A61K 31/505; A61K 31/40; C07D 487/04
[52] U.S. Cl. .............. 514/256; 514/370; 514/377; 514/383; 514/397; 514/402; 514/410; 544/322; 544/328; 544/331; 548/181; 548/233; 548/255; 548/266; 548/336; 548/348; 548/422
[58] Field of Search .............. 548/181, 233, 255, 266, 548/336, 348, 422; 514/256, 370, 377, 383, 397, 402, 410; 544/322, 328, 331

[56] References Cited

U.S. PATENT DOCUMENTS 4,487,769 12/1984 Vyas et al. .................. 548/422 X Primary Examiner—Donald G. Daus
Assistant Examiner—William A. Teoli, Jr.
Attorney, Agent, or Firm—Wolder, Gross & Yavner

[57] ABSTRACT

Mitomycin derivatives having potent antitumor activity having the formula:

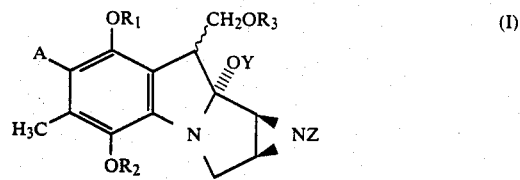

wherein

A is ON— or $R_4N=N$—[wherein $R_4$ is selected from

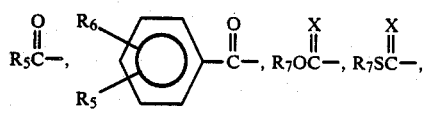

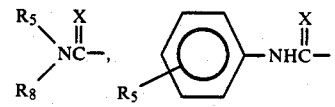

and optionally substituted heterocyclic groups (wherein $R_5$ and $R_8$ are each independently selected from hydrogen, lower alkyl and lower cycloalkyl; $R_6$ is selected from hydrogen, halogen, hydroxy, lower alkoxy, amino and nitro; $R_7$ is selected from lower alkyl and lower cycloalkyl; and X is selected from oxygen, sulphur and imino)];

$R_1$ and $R_2$ are each independently selected from hydrogen, lower alkyl, lower cycloalkyl, optionally substituted aralkyl, optionally substituted alkanoyl, optionally substituted arylcarbonyl, optionally substituted alkanesulfonyl, arylsulfonyl and aralkylsulfonyl;

$R_3$ is hydrogen or carbamoyl;

Y is hydrogen or methyl;

Z is selected from hydrogen, methyl and acetyl;

and ⋯ is an α or β bond.

15 Claims, No Drawings

MITOMYCIN DERIVATIVES AS ANTILEUKEMIA AGENTS

The present invention relates to novel mitomycin derivatives having antitumour activity.

Mitomycins are known as antibodies having, in general, antibacterial and antitumour activities. Examples of typical mitomycin analogues include mitomycin A, mitomycin B, Mitomycin C and porfiromycin, which are referred to in the Merck Index, 10th Edition, mitomycin D and mitomycin E, which are disclosed in JP-A No. 1222797/79, mitomycin F and mitomycin J, which are disclosed in JP-A No. 45322/80, etc. These mitomycins have the chemical structures shown in the following Table 1 and may be obtained by culturing a microorganism of the species *Streptomyces caespitosus*.

TABLE 1
Chemical structures of typical mitomycins

|  | $S_A$ | 9~10 | Y' | Z' |
|---|---|---|---|---|
| Mitomycin A | $OCH_3$ | ◄ | $CH_3$ | H |
| B | $OCH_3$ | ~ | H | $CH_3$ |
| C | $NH_2$ | ◄ | $CH_3$ | H |
| D | $NH_2$ | ‖‖‖ | H | $CH_3$ |
| E | $NH_2$ | ‖‖‖ | $CH_3$ | $CH_3$ |
| F | $OCH_3$ | ◄ | $CH_3$ | $CH_3$ |
| J | $NH_2$ | ‖‖‖ | H | $CH_3$ |
| Porfiromycin | $NH_2$ | ◄ | $CH_3$ | $CH_3$ |

The absolute configurations are disclosed in the Journal of the American Chemical Society, 105, 7199 (1983).

Further, 10-decarbamoylmitomycins are disclosed in the Journal of Medicinal Chemistry, 14, 109 (1971).

Among these mitomycin compounds, mitomycin C is widely used for clinical purposes in view of its especially high antitumour activity. Meanwhile, various derivatives of mitomycin have been prepared to increase antitumour activity and/or decrease high toxicity, in particular against bone marrow.

Thus, for example, certain known derivatives of mitomycin contain a substituted amino group at the 7th position. However, only JP-A No. 169481/85 discloses mitomycin analogues in which the 7-amino group is substituted by a group linked through an atom other than carbon. More particularly, this prior art literature discloses mitomycin analogues in which the 7-amino group is substituted, for example, by a methanesulfonylamino group (in Example 5) or a dimethylphosphorylamino group viz. $(C_2H_5)_2P(=S)NH$—(in Example 14). However, mitomycin analogues in which the 7-amino group is modified with an O-linked substituent have not previously been reported.

The present invention now provides novel mitomycin derivatives in which the 7-group is a nitro group or an amino group with a double bond N-linked substituent whereby the quinone ring is converted into a dihydroquinone ring.

The present invention thus provides mitomycin derivatives having excellent antitumour activity and having the formula:

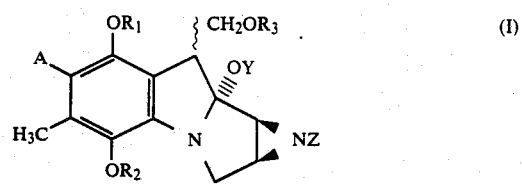

wherein A is ON— or $R_4N=N$— [wherein $R_4$ is selected from

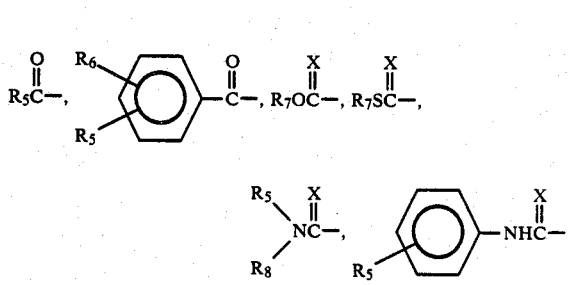

and optionally substituted heterocyclic groups (wherein $R_5$ and $R_8$ are each independently selected from hydrogen, lower alkyl and lower cycloalkyl; $R_6$ is selected from hydrogen, halogen, hydroxy, lower alkoxy, amino and nitro; $R_7$ is selected from lower alkyl and lower cycloalkyl; and X is selected from oxygen, sulphur and imino;

$R_1$ and $R_2$ are each independently selected from hydrogen, lower alkyl, lower cycloalkyl, optionally substituted aralkyl, optionally substituted alkanoyl, optionally substituted arylcarbonyl, optionally substituted alkanesulfonyl, arylsulfonyl and aralkylsulfonyl;

$R_3$ is hydrogen or carbamoyl;

Y is hydrogen or methyl;

Z is selected from hydrogen, methyl and acetyl;

and ~ is an $\alpha$ or $\beta$ bond.

Hereinafter, the compounds of formula (I) are designated as Compounds (I) and compounds of other formulae are designated similarly.

With regard to the definition of $R_5$, $R_7$, $R_8$, $R_1$ and $R_2$ in formula (I), lower alkyl groups may be straight or branched alkyl groups having 1-6 carbon atoms such as, for example, methyl, ethyl, n-propyl, isopropyl, n-butyl, isobutyl, sec-butyl, tert-butyl, n-pentyl, neopentyl, n-hexyl groups and the like, and lower cycloalkyl groups may be cycloalkyl groups having 3-6 carbon atoms such as, for example, cyclopropyl, cyclopentyl, cyclohexyl groups and the like.

With regard to the definition of $R_6$ in formula (I), lower alkoxy groups may be straight or branched alkoxy groups having 1-6 carbon atoms such as, for example, methoxy, ethoxy, isopropoxy, n-butoxy groups and the like.

With regard to the definition of $R_4$, heterocyclic groups are exemplified by imidazolyl, imidazolinyl, thiazolyl, thiazolinyl, oxazolyl, oxazolinyl, triazolinyl and pyrimidyl groups. These heterocyclic groups may be substituted, for example, by lower alkyl groups referred to in the definition of $R_5$, $R_7$, $R_8$, $R_1$ and $R_2$.

With regard to the definition of $R_1$ and $R_2$, optionally substituted aralkyl groups may be, for example, phenethyl, diphenylmethyl, trityl and benzyl groups optionally substituted by 1 or 2 groups each independently selected from lower alkoxy (referred to in the definition of $R_6$), halogen atoms (for example, chlorine and fluorine atoms) as well as nitro, cyano and lower alkyl groups (referred to in the definition of $R_5$, $R_7$, $R_8$, $R_1$ and $R_2$).

With regard to the definition of $R_1$ and $R_2$ lower alkanoyl, which may be unsubstituted or substituted, may be straight or branched alkanoyl groups having 1-6 carbon atoms such as, for example, formyl, acetyl, propionyl, n-butyryl, isobutyryl, n-pentanoyl and n-hexanoyl, which may be substituted with halogen atoms such as, for example, chlorine and fluorine atoms. Preferred examples of substituted lower alkanoyl groups include trichloroacetyl, trifluoroacetyl groups and the like.

With regard to the definition of $R_1$ and $R_2$ aryl groups, which may be unsubstituted or substituted, are exemplified by phenyl and naphthyl groups. These groups may be substituted with 1 or 2 groups, which may be the same or different, selected from lower alkoxy (referred to in the definition of $R_6$), halogen (for example, chlorine and fluorine), nitro, cyano and lower alkyl (referred to in the definition of $R_5$, $R_7$, $R_8$, $R_1$ and $R_2$) and the like.

With regard to the definition of $R_1$ and $R_2$, lower alkanesulfonyl groups are exemplified by straight or branched alkanesulfonyl groups having 1-6 carbon atoms, and the substituents are exemplified by halogen atoms such as, for example, chlorine and fluorine atoms. Preferred examples of optionally substituted lower alkanesulfonyl groups include methanesulfonyl, ethanesulfonyl, isopropanesulfonyl, n-butanesulfonyl, n-hexanesulfonyl, trichloromethanesulfonyl and trifluoromethanesulfonyl groups.

With regard to the definition of $R_1$ and $R_2$, arylsulfonyl groups are exemplified by benzenesulfonyl and p-toluenesulfonyl. Aralkylsulfonyl groups are exemplified by benzylsulfonyl groups.

Compounds (I-1) (viz. a compound of formula (I) wherein $R_1 = R_2 = H$) may be prepared by reacting a mitomycin compound of formula (II):

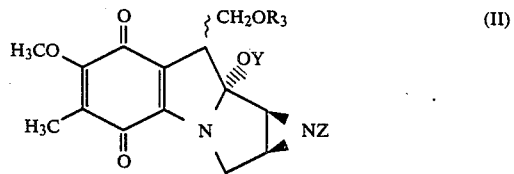

(wherein $R_3$, Y, Z and ⁓⁓⁓ are as hereinbefore defined in formula I) with one member selected from hydroxylamine, acid addition salts thereof, compounds of formula (III):

R_4NHNH_2    (III)

(wherein $R_4$ is as hereinbefore defined in formula I) and acid addition salts thereof, in an inert solvent. If desired, the reaction may be carried out in the presence of a base.

Examples of suitable acid addition salts of hydroxylamine or acid addition salts of compounds (III) include inorganic acid salts such as hydrochloride and hydrogen bromide; and organic acid salts such as acetate, oxalate and p-toluenesulfonate. Hydroxylamine, compounds (III) and acid addition salts thereof may preferably be used in a ratio of 1-3 moles per mole of Compounds (II). Where the acid addition salt of hydroxylamine or of Compound (III) is used, a base is used to liberate hydroxylamine or Compound (III). Examples of suitable bases include inorganic bases such as sodium carbonate, potassium carbonate, sodium bicarbonate, sodium hydroxide, potassium hydroxide and lithium hydroxide; tertiary amines such as pyridine, 4-dimethylaminopyridine, triethylamine and N,N-dimethylaniline; alkali metal alkoxides such as sodium methoxide, sodium ethoxide, potassium methoxide and potassium ethoxide, and the like.

In some cases where a Compound (II) is reacted with free Compound (III), the use of a base is preferred to promote the reaction with better results.

Suitable inert solvents are exemplified by lower alkanols such as methanol, ethanol and isopropanol; acetonitrile, dimethylformamide, dimethylsulfoxide, tetrahydrofuran and water, any of which may be used alone or in admixture.

The reaction may preferably be carried out at a temperature of from 0° C. to 40° C., for example at ambient temperature, and is usually continued for a period of from 10 minutes to 10 hours.

After completion of the reaction, the Compounds (I) may be isolated by conventional techniques such as, for example, extraction, chromatography, recrystallization and various other methods known for the isolation and purification of reaction products.

In addition to the formula (I), it is believed that Compounds (I-1) may exist at least partially as the tautomer of formula (IV):

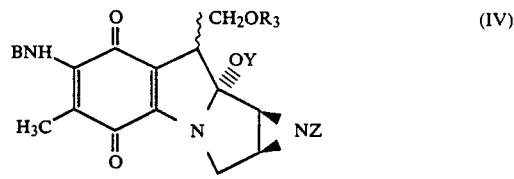

[wherein B is selected from hydroxy and $R_4NH$, (wherein $R_4$ is as hereinbefore defined in formula I) and $R_3$, Y, Z and ⁓⁓⁓ are as hereinbefore defined in formula I)].

For example, the results obtained from $^1H$- and $^{13}C$-NMR (in $d_6$-dimethylsulfoxide) of a compound prepared by the method described in Example 1 indicate that this compound has the structure of formula (I). However, in general, tautomerism is liable to occur at different production ratios, which may vary, depending upon various factors such as the structure, conditions for measuring NMR and the like. Thus, the present invention also extends to Compounds (IV) as tautomers of compounds of formula (I) (wherein $R_1 = R_2 = H$)

Compounds (I-2) [viz. compounds of formula (I) wherein $R_1$ and $R_2$ are each independently selected from hydrogen, lower alkyl, lower cycloalkyl and optionally substituted aralkyl (except where both $R_1$ and $R_2$ are hydrogen)] may be prepared by reacting a Compound (I-1) with an alkylating agent represented by the formulae:

$R_9$-Hal; $(R_9)_2SO_4$, $CH_2N_2$ and $(R_9)_3OBF_4$ (in these formulae, $R_9$ is selected from lower alkyl, lower cycloalkyl and optionally substituted aralkyl) in an inert solvent in the presence of a base.

Where the ratio of alkylating agent used is 0.8-1.2 moles per mole of Compound (I-1), only $R_2$ of the resultant product is alkylated, while both $R_1$ and $R_2$ of the product may be alkylated by using the alkylating agent in 2-4 molar ratio.

Suitable bases are exemplified by inorganic bases such as sodium hydride, lithium hydride, sodium carbonate, potassium carbonate, sodium bicarbonate and silver oxide and organic bases such as sodium methoxide, sodium ethoxide, potassium methoxide, potassium ethoxide, potassium-tert-butoxide, n-butyl lithium, sec-butyl lithium, phenyl lithium and lithium diisopropylamide. Usually an equimolar amount of base to alkylating agent is used.

Suitable inert solvents are exemplified by lower alkanols such as methanol, ethanol, isopropanol and tert-butanol, acetonitrile, dimethylformamide, dimethylsulfoxide, tetrahydrofuran and the like, any of which may be used alone or in admixture.

Compounds (I-3) [viz. compounds of formula (I), wherein $R_1$ and $R_2$ are each independently selected from hydrogen, optionally substituted lower alkanoyl and optionally substituted arylcarbonyl (except where both $R_1$ and $R_2$ are hydrogen); and Z is acetyl or methyl] may be prepared by reacting a Compound (I-1) wherein Z is acetyl or methyl, with a reactive derivative of carboxylic acid (hereinafter referred to as acylating agent) of the formula:

$$R_{10}\text{-OH}$$

(wherein $R_{10}$ is selected from optionally substituted lower alkanoyl and optionally substituted arylcarbonyl) in an inert solvent in the presence of a base.

Examples of suitable acylating agents which may be used include acid halogenated products such as acid chlorides and acid bromides, acid anhydrides and the like. Where the ratio of acylating agent used is 0.8-1.2 moles per mole of Compound (I-1), only $R_2$ of the resultant product is acylated, while both $R_1$ and $R_2$ of the product may be acylated by using the acylating agent in 2-4 molar ratio. Suitable bases for this purpose are exemplified by inorganic bases such as sodium hydride, lithium hydride, sodium carbonate, potassium carbonate, sodium bicarbonate and silver oxide and organic bases such as sodium methoxide, sodium ethoxide, potassium methoxide, potassium ethoxide, potassium tert-butoxide, n-butyl lithium, sec-butyl lithium, phenyl lithium, lithium diisopropylamide, triethylamine, pyridine, N,N-dimethylaniline and 4-dimethylaminopyridine. Usually an equimolar amount of base to acylating agent is used.

Suitable inert solvents include, for example, acetonitrile, dimethylformamide, dimethylsulfoxide, tetrahydrofuran and the like. In the cases where an acid anhydride is used as the acylating agent, for example, triethylamine, pyridine, N,N-dimethylaniline and the like it may serve, if desired, as both base and inert solvent.

Compounds (I-3') [viz. Compounds (I), wherein $R_1$ and $R_2$ are each independently selected from hydrogen, optionally substituted lower alkanoyl and optionally substituted lower arylcarbonyl (except where both $R_1$ and $R_2$ are hydrogen) and Z is hydrogen] may be prepared by reacting a Compound (I-3'') (viz. Compounds (I) wherein Z is acetyl) with an aqueous solution of hydroxylamine in a lower alkanol. The ratio of hydroxylamine used is, for example, 1-2 moles per mole of Compound (I-3''). Examples of lower alkanols include methanol, ethanol, isopropanol and the like.

Compounds (I-4) [viz. Compounds (I), wherein $R_1$ and $R_2$ are each independently selected from hydrogen, optionally substituted alkanesulfonyl, arylsulfonyl and aralkylsulfonyl (except where both $R_1$ and $R_2$ are hydrogen] may be prepared by reacting a Compound (I-1) with a reactive derivative of sulfonic acid (hereinafter referred to as sulfonating agent) of the formula:

$$R_{11}\text{-OH}$$

(wherein $R_{11}$ is selected from optionally substituted lower alkanesulfonyl, arylsulfonyl and aralkylsulfonyl) in an inert solvent in the presence of a base.

Examples of sulfonating agents which may preferably be used include acid halogenated products such as acid chloride and acid bromide, acid anhydrides and the like. Where the ratio of sulfonating agent used is 0.8-1.2 moles per mole Compound (I-1), only $R_2$ may be sulfonated, while both $R_1$ and $R_2$ may be sulfonated by using the sulfonating agent in 2-4 molar ratio. Suitable bases and inert solvents which may be used for this purpose are the same as those suitable for the acylation reaction hereinbefore disclosed. In the case where an acid anhydride is used for sulfonation, for example, triethylamine, pyridine, N,N-dimethylaniline and the like may be used as both base and solvent.

Preferably, reactions for the above-mentioned alkylation, acylation, partial deacylation or sulfonation may be carried out at a temperature of from 0° C. to ambient, and usually continued for a period of several to several tens of hours.

After completion of reaction, Compounds (I-2), (I-3) and (I-4) may be isolated by conventional techniques such as, for example, extraction, chromatography, recrystallization and the like.

As shown hereinafter, Compounds (I) exhibit excellent antitumour activities. Certain Compounds (I) exhibit greater C.I. values than that of mitomycin C. This fact suggests that Compounds (I) may be administered at a greater dose than mitomycin C. Moreover, as is shown hereinafter the ratios of $WBC_{4000}$ to $ED_{50}$ of Compounds (I) are, in general, greater than the corresponding ratio of mitomycin C. This fact suggests their toxicities against bone marrow are superior to that of mitomycin C calculated on the doses resulting in the same $ED_{50}$.

Thus, Compounds (I) may be used for the preparation of antitumour pharmaceutical compositions, comprising as active ingredient an effective amount of a Compound (I), in association with at least one pharmaceutically acceptable carrier and/or adjuvant. Thus such compositions may contain e.g. diluents, excipients, disintegrating agents, binders, lubricants, formulation bases and the like conventionally used in pharmacy.

The Compounds (I) also have utility as intermediates for the preparation of other compounds having antitumour activity.

Compounds (I) may be administered in various forms. For example, when used for parenteral injection, Compounds (I) may be dissolved in liquid carriers conventionally used in the art (for example, ethanol), to which, if desired, a surfactant, solubilizing agent or the like may be added. The ethanol solution may be mixed with e.g. distilled water for injection, physiological saline, distilled water containing fructose, mannitol etc. or the like conventionally used for such purposes. In this case, the mixture may be used with or without removal of ethanol.

It is also possible to use Compounds (I) in the form of a hypodermic powder which may be obtained by freeze-drying the ethanol solution or by mixing Compounds (I) with sodium chloride. In use, the powder is suitably dissolved. The injection may preferably be intravenous, although it is possible to administer e.g. by the intramuscular, intra-arterial, abdominal, or pleural routes.

Compositions for oral administration may be prepared in conventional manner by formulating Compounds (I) in association with suitable excipients, disintegrating agents, binders, lubricants and the like into tablets, granules or powders. Suppositories may be obtained by mixing Compounds (I) with suitable suppository bases in conventional manner.

The optimum dose may vary, depending upon the particular Compound (I), the age of the patient, the symptoms and the like. However, one may e.g. administer Compounds (I) at a dosage in the range of 2–150 mg/60 kg.

Our invention is illustrated in the following Examples and formulations. Mass spectrometry was carried out by the FAB (Fast Atom Bombardment) method.

In the Examples, the nomenclature used is illustrated by the compound of Example 1 having the following structure and designation:

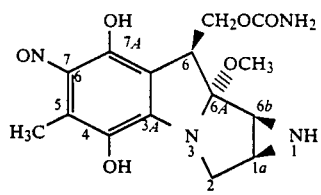

[1aS-(1aα,8β,8aα,8bα)]-8-{[(aminocarbonyl)oxy]methyl}-4,7-dihydroxy-1,1a,2,8,8a,8b-hexahydro-8a-methoxy-5-methyl-6-nitroso-azirino[2′,3′:3,4]pyrrolo[1,2-a]indole.

Conveniently the following Table 2 indicates the structure of various compounds prepared by the methods of Examples 1–35 described hereinafter.

TABLE 2

| Compounds (Example No.) | A | $R_1$ | $R_2$ | $R_3$ | 8 9 ⁓ Y | Z |
|---|---|---|---|---|---|---|
| 1 | ON | H | H | $CONH_2$ | ◂ $CH_3$ | H |
| 2 | ON | H | H | $CONH_2$ | ◂ $CH_3$ | H |
| 3 | ON | H | H | $CONH_2$ | $H$ | $CH_3$ |
| 4 | ON | H | H | H | ◂ $CH_3$ | H |
| 5 | ON | H | H | H | ◂ $CH_3$ | $CH_3$ |
| 6 | ON | H | $CH_3$ | $CONH_2$ | ◂ $CH_3$ | H |
| 7 | ON | H | $CH_3$ | $CONH_2$ | ◂ $CH_3$ | $CH_3$ |
| 8 | ON | $CH_3$ | $CH_3$ | $CONH_2$ | ◂ $CH_3$ | H |
| 9 | ON | H | $CH_3$ | H | ◂ $CH_3$ | H |
| 10 | ON | H | $CH_3$ | $CONH_2$ | ⫼ H | $CH_3$ |
| 11 | ON | H | $COCH_3$ | $CONH_2$ | ◂ $CH_3$ | $COCH_3$ |
| 12 | ON | H | $(CH_3)_2CH$ | $CONH_2$ | ◂ $CH_3$ | H |
| 13 | ON | H | $(CH_3)_2CHCH_2$ | $CONH_2$ | ◂ $CH_3$ | H |
| 14 | ON | H | C₆H₅—$CH_2$ | $CONH_2$ | ◂ $CH_3$ | H |
| 15 | ON | H | $CH_3$—C₆H₄—SO₂— | $CONH_2$ | ◂ $CH_3$ | H |
| 16 | ON | $CH_3$—C₆H₄—SO₂— | $CH_3$—C₆H₄—SO₂— | $CONH_2$ | ◂ $CH_3$ | H |
| 17 | C₆H₅—C(O)—CN=N | H | H | $CONH_2$ | ◂ $CH_3$ | H |
| 18 | $CH_3C(O)N=N$ | H | H | $CONH_2$ | ◂ $CH_3$ | H |

TABLE 2-continued

Structure (I):
- Benzene ring with substituents: $OR_1$ (top), A (left), $CH_3$ (bottom left), $OR_1$ (bottom), linked via N to a pyrrolidine fused cyclopropane bearing $NZ$; side chain at position 8–9 with $CH_2OR_3$ and $OY$.

| Compounds (Example No.) | A | $R_1$ | $R_2$ | $R_3$ | 8~9 | Y | Z |
|---|---|---|---|---|---|---|---|
| 19 | 4-H₂N-C₆H₄-C(=O)-N=N- | H | H | CONH₂ | ◄ | CH₃ | H |
| 20 | 4-HO-C₆H₄-C(=O)-N=N- | H | H | CONH₂ | ◄ | CH₃ | H |
| 21 | C₆H₅-C(=O)-N=N- | H | H | CONH₂ | ◄ | CH₃ | CH₃ |
| 22 | C₆H₅-C(=O)-N=N- | H | H | CONH₂ | ◄ | CH₃ | CH₃ |
| 23 | piperazinyl-C(=O)-N=N- | H | H | CONH₂ | ◄ | CH₃ | H |
| 24 | CH₃O-C(=O)-N=N- | H | H | CONH₂ | ◄ | CH₃ | H |
| 25 | H₂N-C(=O)-N=N- | H | H | CONH₂ | ◄ | CH₃ | H |
| 27 | C₆H₅-C(=O)-N=N- | H | CH₃ | CONH₂ | ◄ | CH₃ | H |
| 28 | 2-HO-C₆H₄-C(=O)-N=N- | H | H | CONH₂ | ◄ | CH₃ | H |
| 29 | C₆H₅-C(=O)-N=N- | H | H | CONH₂ | ||||  | H | CH₃ |
| 30 | (CH₃)₃C-C(=O)-N=N- | H | H | CONH₂ | ◄ | CH₃ | H |
| 31 | H₃CS-C(=S)-N=N- | H | H | CONH₂ | ◄ | CH₃ | H |
| 32 | H₂N-C(=S)-N=N- | H | H | CONH₂ | ◄ | CH₃ | H |

TABLE 2-continued

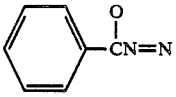

| Compounds (Example No.) | A | R$_1$ | R$_2$ | R$_3$ | 8~9 | Y | Z |
|---|---|---|---|---|---|---|---|
| 33 | [phenyl-C(=O)-CN=N] | H | CH$_3$ | CONH$_2$ | | H | CH$_3$ |
| 34 | ON | H | COCH$_3$ | CONH$_2$ | ◄ | CH$_3$ | H |
| 35 | ON | H | C$_2$H$_5$ | CONH$_2$ | ◄ | CH$_3$ | H |

EXAMPLE 1

Preparation of [1aS-(1aα, 8β, 8aα,8bα)]-8-{[(aminocarbonyl)oxy]methyl}-4,7-dihydroxy-1, 1a, 2, 8, 8a, 8b-hexahydro-8a-methoxy-5-methyl-6-nitroso-azirino [2',3':3,4]pyrrolo[1,2-a]indole 2.38 g of hydroxylamine hydrochloride is dissolved in water (10 ml), to which is then added anhydrous sodium carbonate in limited amounts (2.18 g in total) while stirring. This solution is added to methanol (400 ml), in which mitomycin A (6.00 g) has been dissolved. The mixture is stirred at ambient temperature for 2 hours. After removal of the solvent by evaporation under reduced pressure, the residual material is subjected to silica gel chromatography using chloroform/methanol (9:1 v/v) as a solvent system for purification. 5.12 g of the desired compound was obtained with a yield of 86.5%.

$^1$H-NMR (d$_6$-DMSO)δ; 2.06 (3H, s), 2.76 (1H, dd), 2.89 (1H, d), 3.16 (3H, s), 3.45 (1H, dd), 3.53 (1H, dd), 4.09 (1H, dd), 4.17 (1H, d), 4.63 (1H, dd), 6.55 (2H, br), 10.17 (1H, s), 19.17 (1H, s)

$^{13}$C-NMR (d6-DMSO) δ; 9.5, 31.2, 35.5, 41.6, 49.3, 49.6, 60.0, 105.9, 107.7, 120.9, 139.0, 148.2, 156.5, 160.1, 169.0

IR (KBr) cm$^{-1}$; 3400, 2940, 1705, 1590, 1480, 1330, 1210, 1060

MASS 351 (C$_{15}$H$_{18}$N$_4$O$_6$ : Molecular weight 350.34)

EXAMPLE 2

Preparation of [1aS-(1aα, 8β, 8aα, 8bβ)]-8-{[(aminocarbonyl)oxy]methyl}-4,7-dihydroxy-1,5-dimethyl-1,1a,2,8-,8a,8b-hexahydro-8a-methoxy-6-nitroso-azirino [2',3':3,4]pyrrolo [1,2-a]indole In a similar manner to that described in Example 1, hydroxylamine hydrochloride (0.038 g), anhydrous sodium carbonate (0.033 g) and mitomycin F (0.100 g) are used to obtain the desired product (0.098 g; yield 87.0%).

$^1$H-NMR(d6-DMSO) δ; 2.05 (3H, s), 2.26 (3H, s), 2.36 (1H, dd), 2.40 (1H, d), 3.22 (3H, s), 3.58 (1H, dd) 3.67 (1H, dd), 4.10 (1H, d), 4.15 (1H, dd), 4.68 (1H, dd), 6.40 (2H, br), 9.98 (1H, s), 19.05 (1H, s)

IR (KBr) cm$^{-1}$; 3400, 2950, 1705, 1590, 1480, 1340, 220, 1060

MASS 365 (C$_{16}$H$_{20}$N$_4$O$_6$ : Molecular weight 364.36)

EXAMPLE 3

Preparation of [1aS-(1aα,8α, 8aα, 8bα]-8-{[(aminocarbonyl)oxy]methyl}-1,5-dimethyl-1,1a,2,8,8a,8b-hexahydro-6-nitroso-4,7,8a-trihydroxy-azirino [2',3':3,4]pyrrolo[1,2-a]indole In a similar manner to that described in Example 1, hydroxylamine hydrochloride (0.49 g), anhydrous sodium carbonate (0.45 g) and mitomycin B (1.20 g) are used to obtain the desired product (0.88 g; yield 73.2%).

$^1$H-NMR (d$_6$-DMSO) δ; 2.04 (3H, s), 2.24 (3H, s), 2.35 (1H, dd), 2.49 (1H, d), 3.63 (1H, dd), 3.72 (1H, dd), 4.08 (1H, d), 4.15 (1H, dd), 4.74 (1H, dd), 6.38 (2H, br), 6.62 (1H, br), 9.52 (1H, s), 19.34 (1H, s)

IR (KBr) cm$^{-1}$; 3400, 2950, 1705, 1595, 1480, 1345, 1220, 1055

MASS 351 (C$_{15}$H$_{18}$N$_4$O$_6$ : Molecular weight 350.34)

EXAMPLE 4

Preparation of [1aS-(1aα, 8β, 8aα, 8bα)]-4,7-dihydroxy-1,1a,2,8,8a,8b-hexahydro-8-hydroxymethyl-8a-methoxy-5-methyl-6-nitroso-azirino [2',3':3,4]pyrrolo[1,2-a]indole In a similar manner to that described in Example 1, decarbamoylmitomycin A (J. Medicinal Chemistry, Vol. 14, page 109, 1971; 0.13 g), hydroxylamine hydrochloride (0.059 g) and anhydrous sodium carbonate (0.054 g) are used to obtain the desired product (0.11 g; yield 85.3%).

$^1$H-NMR (CDCl$_3$/CD$_3$OD) δ; 2.19 (3H, s), 2.90 (1H, dd), 2.95 (1H, d), 3.23 (3H, s), 3.44 (1H, dd), 3.63 (1H, dd), 3.98 (1H, dd), 4.04 (1H, dd), 4.35 (1H, d), 18.76 (1H, s),

IR (KBr) cm$^{-1}$; 3450, 2950, 1595, 1530, 1485, 1380, 1330, 1210, 1030

MASS 308 (C$_{14}$H$_{17}$N$_3$O$_5$ : Molecular weight 307.31)

EXAMPLE 5

Preparation of [1aS-(1aα, 8β, 8aα, 8bα)]-4,7-dihydroxy-1,5-dimethyl-1,1a,2,8,8a,8b-hexahydro-8-hydroxymethyl-8a-methoxy-6-nitroso-azirino [2',3':3,4]pyrrolo [1,2-a]indole In a similar manner to that described in Example 1, the desired product (0.21 g; yield 69.5%) is obtained by the use of decarbamoylmitomycin F (Chemical Abstracts, vol. 74, 99920n, 1971) (0.30 g),hydroxylamine hydrochloride (0.14 g) and anhydrous sodium carbonate (0.10 g).

$^1$H-NMR (CDCl$_3$/CD$_3$OD) δ; 2.10 (3H, s), 2.31 (3H, s), 2.37 (1H, dd), 2.40 (1H, d), 3.21 (3H, s), 3.39 (1H, dd), 3.58 (1H, dd), 3.94 (1H, dd), 4.01 (1H, dd), 4.35 (1H, d), 18.77 (1H, s)

IR (KBr) cm$^{-1}$; 3450, 2950, 1590, 1530, 1480, 1370, 1210, 1030

MASS 322 (C$_{15}$H$_{19}$N$_3$O$_5$ : Molecular weight 321.33)

EXAMPLE 6

Preparation of [1aS-(1aα, 8β, 8aα, 8bα)]-8-{[(aminocarbonyl)oxy]methyl}-4,8a-dimethoxy-1,1a,2,8,8a,8b-hexahydro-7-hydroxy-5-methyl-6-nitroso-azirino 2,'3':3,4)-pyrrolo[1,2-a]indole A compound obtained by the method of Example 1 (3.00 g) is dissolved in a mixture of dimethylformamide (50 ml) and tert-butanol (50 ml). After addition of tert-butoxy potassium (0.86 g), the mixture is stirred at ambient temperature for 20 minutes. Then methyl iodide (0.69 ml) is added to the solution, followed by stirring at ambient temperature for 1.5 hours. The solvent is removed from the solution by evaporation under reduced pressure to give an oily material, to which are added chloroform and water. The extracted chloroform layer is dried by using anhydrous sodium sulfate. After removal of chloroform by evaporation under reduced pressure, the residual material is subjected to silica gel chromatography by using a solvent system of chloroform/methanol (15:1 v/v) to yield the desired product (1.32 g) with a yield of 42.3%.

$^1$H-NMR(CDCl$_3$) δ; 2.30 (3H, s), 2.87 (1H, dd), 2.98 (1H, d), 3.24 (3H, s), 3.57 (1H, dd), 3.72 (3H, s), 3.74 (1H, dd), 4.24 (1H, d), 4.51 (1H, dd), 4.84 (1H, dd), 19.01 (1H, s)

IR (KBr) cm$^{-1}$, 3400, 2930, 1715, 1605, 1480, 1335, 1220, 1065

MASS 365 (C$_{16}$H$_{20}$N$_4$O$_6$: Molecular weight 364.37)

EXAMPLE 7

Preparation of [1aS-(1aα, 8α, 8aα, 8bα)]-8-{[(aminocarbonyl)oxy]methyl}-4,8a-dimethoxy-1,5-dimethyl-1,1a,2,8-,8a,8b-hexahydro-7-hydroxy-6-nitroso-azirino-[2',3':3,4]-pyrrolo[1,2-a]indole A compound prepared by the method of Example 2 (0.30 g) and tert-butoxy potassium (0.10 g) as well as methyl iodide (0.07 ml) are treated in a similar manner to that described in Example 6 to obtain the desired product (0.12 g; yield 38.7%).

$^1$H-NMR (CDCl$_3$) δ; 2.28 (3H, s), 2.29 (3H, s), 2.36 (1H, dd), 2.38 (1H, d), 3.22 (3H, s), 3.51 (1H, dd), 3.66 (1H, dd), 3.72 (3H, s), 4.22 (1H, d), 4.32 (1H, dd), 4.78 (2H, br), 4.84 (1H, dd), 19.03 (1H, s)

IR (KBr) cm$^{-1}$; 3400, 2950, 1720, 1605, 1480, 1340, 1215, 1150, 1055

MASS 379 (C$_{17}$H$_{22}$N$_4$O$_6$: Molecular weight 378.40)

EXAMPLE 8

Preparation of [1aS-(1aα, 8β, 8aα, 8bα)]-8-{[(aminocarbonyl)oxy]methyl}-1,1a,2,8,8a,8b-hexahydro-5-methyl-6-nitroso-4,7,8a-trimethoxy-azirino[2',3':3,4]pyrrolo[1,2-a]indole 0.30 g of a compound prepared by the method of Example 1 is dissolved in DMF (15 ml). To this solution is added sodium hydride (0.069 g; 60%; oily substance). The mixture is stirred at ambient temperature for 30 minutes. Then methyl iodide (0.12 ml) is added to the solution, which is further stirred at ambient temperature for one hour. The solvent is removed from the solution by evaporation under reduced pressure to give an oily material. The oily material is extracted with addition of chloroform and water. The extracted chloroform layer is dried by using anhydrous sodium sulfate, and chloroform is removed by evaporation under reduced pressure. The residual material is subjected to silica gel chromatography using a solvent system of chloroform/methanol (15:1 v/v) to obtain 0.10 g of the desired product with a yield of 30.8%.

$^1$H-NMR (d$_6$-DMSO) δ; 2.14 (3H, s), 2.44 (1H, dd), 2.48 (1H, d), 3.38 (3H, s), 3.49 (1H, dd), 3.66 (3H, s), 3.88 (1H, dd), 3.95 (1H, d), 4.06 (3H, s), 4.49 (1H, dd), 4.55 (1H, dd), 6.55 (2H, br)

IR (KBr) cm$^{-1}$; 3450, 2940, 1705, 1620, 1600, 1540, 1450, 1330, 1220, 1050

MASS 379 (C$_{17}$H$_{22}$N$_4$O$_6$: Molecular weight 378.40)

EXAMPLE 9

Preparation of [1aS-(1aα, 8β, 8aα, 8bα)]-4,8a-dimethoxy-1,1a,2,8,8a,8b-hexahydro-7-hydroxy-8-hydroxymethyl-5-methyl-6-nitroso-azirino[2',3':3,4]pyrrolo[1,2-a]indole 0.22 g of a compound obtained by the method of Example 6 is treated by the method disclosed in J. of Medicinal Chemistry, Vol. 14, page 109, 1971 for decarbamoylization. 0.14 g of the desired product is obtained with a yield of 72.7%.

$^1$H-NMR (CDCl$_3$) δ; 2.28 (3H, s), 2,91 (1H, dd), 2.98 (1H, d), 3.30 (3H, s), 3.48 (1H, dd), 3.58 (1H, dd), 3.78 (3H, s), 4.03 (1H, dd), 4.08 (1H, dd), 4.24 (1H, d), 18.90 (1H, s)

IR (KBr) cm$^{-1}$; 3400, 2930, 1600, 1460, 1380, 1205, 1035

MASS 322 (C$_{15}$H$_{19}$N$_3$O$_5$: Molecular weight 321.33)

EXAMPLE 10

Preparation of 1aS-(1aα, 8α, 8aα,8bα)]-8-{[(aminocarbonyl)oxy]methyl}-7,8a-dihydroxy-1,5-dimethyl-1,1a,2,8-,8a,8b-hexahydro-4-methoxy-6-nitroso-azirino [2', 3':3, 4]pyrrolo [1,2-a]indole A compound prepared by the method of Example 3 (0.90 g), tert-butoxy potassium (0.30 g) and methyl iodide (0.22 ml) are treated in a similar manner to that described in Example 6 to obtain the desired product (0.28 g; yield 29.9%).

$^1$H-NMR (CDCl$_3$/CD$_3$OD) δ; 2.24 (3H, s), 2.32 (3H, s), 2.38 (1H, dd), 2.64 (1H, d), 3.60 (1H, dd), 3.70 (3H, s), 3.76 (1H, dd), 4.15 (1H, d), 4.59 (1H, dd), 4.82 (1H, dd), 19.15 (1H, s)

IR (KBr) cm$^{-1}$; 3420, 2950, 1700, 1605, 1520, 1480, 1350, 1060

MASS 365 (C$_{16}$H$_{20}$N$_4$O$_6$: Molecular weight 364.37)

EXAMPLE 11

Preparation of [1aS-(1aα, 8β, 8aα, 8bα)]-1-acetyl-4-acetyloxy-8-{[(aminocarbonyl)oxy]methyl}-1,1a,2,8-,8a,8b-hexahydro-7-hydroxy-8a-methoxy-5-methyl-6-nitroso-azirino[2',3':3,4]pyrrolo[1,2-a]indole N'-acetyl-mitomycin A (disclosed in JP-A No. 18117/65 is treated in a similar manner to that described in Example 1 to prepare [1aS-(1aα,8β,8α,8bα)]-1-acetyl-8-{[(aminocarbonyl)oxy] methyl}-4,7-dihydroxy-1,1a,2,8,8a,8b-hexahydro-8a-methoxy-5-methyl-6-nitroso-azirino 2',3':3,4]pyrrolo [1,2-a]indole, of which 1.03 g is dissolved in pyridine (110 ml). After addition of anhydrous acetic acid (0.3 ml), the mixture is stirred at ambient temperature for 10 hours. The solvent is removed from the solution by evaporation under reduced pressure to give an oily material. This material is subjected to silica gel chromatography using a solvent system of chloroform/methanol (15:1 v/v) to obtain the desired product (1.00 g) with a yield of 87.6%.

$^1$H-NMR (CDCl$_3$) δ: 2.14 (3H, s), 2.32 (3H, s), 2.40 (3H, s), 3.19 (3H, s), 3.30 (1H, dd), 3.48 (1H, dd), 3.53 (1H, d), 3.77 (1H, dd), 4.01 (1H, dd), 4.09 (1H, d), 4.99 (1H, dd), 15.80 (1H, s)

IR (KBr) cm$^{-1}$; 3400, 2950, 1710, 1620, 1480, 1340, 1210, 1190, 1070

MASS 435 (C$_{19}$H$_{22}$N$_4$ O$_8$: Molecular weight 434.40)

EXAMPLE 12

Preparation of [1aS-(1aα,8β,8aα,8bα)]-8-{[(aminocarbonyl) oxy]methyl}-1,1a,2,8,8a,8b-hexahydro-7-hydroxy-4-isopropyloxy-8a-methoxy-5-methyl-6-nitroso-azirino[2',3':3,4]pyrrolo[1,2-a]indole A compound prepared by the method of Example 1 (0.50 g) is dissolved in dimethylformamide (20 ml). After addition of sodium hydride (0.052 g; 60% oily), the solution is stirred for 15 minutes at ambient temperature. Then isopropyl iodide (0.18 ml) is added to the solution, and the solution is stirred for 1.5 hours at ambient temperature. The solvent is removed from the solution by evaporation under reduced pressure to give an oily material, to which are then added chloroform and water. The extracted chloroform layer is dried using anhydrous sodium sulfate in vacuo. The residue is subjected to silica gel chromatography by using a solvent system of chloroform/methanol (30:1 v/v) to obtain the desired product (0.16 g) with a yield of 28.5%

$^1$H-NMR (CDCl$_3$) δ: 1.32 (6H, d), 2.26 (3H, s), 2.85 (1H, dd), 2.98 (1H, d), 3.22 (3H, s), 3.50 (1H, dd), 3.69 (1H, dd), 4.20 (1H, q), 4.28 (1H, d), 4.43 (1H, dd), 4.87 (1H, dd), 5.10 (2H, br), 19.06 (1H, s)

IR (KBr) cm $^{-1}$: 3450, 2950, 1710, 1600, 1480, 1335, 1210, 1060

MASS 393 (C$_{18}$H$_{24}$N$_4$ O$_6$: Molecular weight 392.41)

EXAMPLE 13

Preparation of [1aS-(1aα, 8β, 8aα, 8bα)]-8-{[(aminocarbonyl) oxy]methyl}-1,1a,2,8,8a,8b-hexahydro-7-hydroxy -4-isobutyloxy-8a-methoxy-5-methyl-6-nitroso-azirino[2',3':3,4]pyrrolo[1,2-a]indole A compound (0.50 g) prepared by the method of Example 1, sodium hydride (0.057 g; 60%; oily substance) and isobutyl iodide (0.25 ml) are treated in a similar manner to that described in Example 12 to obtain the desired product (0.11 g) with a yield of 18.1%.

$^1$H-NMR (CDCl$_3$) δ; 1.06 (3H, d), 1.07 (3H, d), 2.07 1H, m), 2.27 (3H, s), 2.86 (1H, dd), 2.99 (1H, d), 3.24 (3H, s), 3.45 (1H, d), 3.51 (1H, dd), 3.65 (1H, d), 3.69 (1H, dd), 4.24 (1H, d), 4.46 (1H, dd), 4.84 (1H, dd), 5.05 (2H, br), 19.05 (1H, s)

IR (KBr) cm$^{-1}$; 3450, 2950, 1710, 1600, 1480, 1340, 1220, 1060

MASS 407 ( C$_{19}$H$_{26}$N$_4$O$_6$: Molecular weight 406.44)

EXAMPLE 14

Preparation of [1aS-(1aα,8β,8aα,8bα)]-8-{[(aminocarbonyl)oxy]methyl-}4-benzyloxy-1,1a,2,8,8a,8b-hexahydro-7-hydroxy-8a-methoxy-5-methyl-6-nitroso-azirino[2',3':3,4]pyrrolo[1.2-a]indole A compound (0.42 g) prepared by the method of Example 1 is dissolved in a mixture of dimethylformamide (9 ml) and tertbutanol (9 ml), to which is further added tert-butoxy potassium (0.12 g) while cooling with ice. The mixture is stirred for 30 minutes. Then benzyl bromide (0.15 ml) is added to the solution while cooling with ice. The solution is stirred for one hour at ambient temperature. To an oily material obtained by removal of the solvent from the solution by evaporation under reduced pressure, chloroform and water are added. The extracted chloroform layer is dried using anhydrous sodium hydride. The residual material is subjected to silica gel chromatography using a solvent system of chloroform/methanol (20:1 v/v) to obtain the desired product (0.09 g) with a yield of 17.5%.

$^1$H-NMR (CDCl$_3$) δ; 2.27 (3H, s), 2.80 (1H, dd), 2.95 (1H, d), 3.17 (3H, s), 3.37 (1H, dd), 3.71 (1H, dd), 4.23 (1H, d), 4.52 (1H, dd), 4.70 (2H, br), 4.85 (2H, s), 4.86 (1H, dd), 7.39 (5H, s), 18.99 (1H, s)

IR (KBr) cm$^{-1}$; 3450, 2950, 1700, 1630, 1590, 1480, 1320, 1205, 1060

MASS 441 (C$_{22}$H$_{24}$N$_4$O$_6$: Molecular weight 440.46)

EXAMPLE 15

Preparation of [1aS-(1aα,8β,8aα,8bα)]-8-{[(aminocarbonyl)-oxy]methyl}-1,1a,2,8,8a,8b-hexahydro-7-hydroxy-8a-methoxy-5-methyl-6-nitroso-4-[(p-toluenesulfonyl)oxy]azirino[2',3':3,4]pyrrolo[1,2-a]indole A compound (0.33 g) prepared by the method of Example 1 is dissolved in tetrahydrofuran (40 ml). To this solution are added triethylamine (0.12 ml) and p-toluenesulfonic acid chloride (0.15 g) while cooling with ice. The mixture is stirred at the same temperature for 30 minutes. The reaction solution is poured into a saturated solution of sodium chloride. Tetrahydrofuran layer is dried by using anhydrous sodium sulfate and concentrated under reduced pressure. The residual material is subjected to silica gel chromatography using a solvent system of chloroform/methanol (30:1 v/v) to obtain the desired product (0.11 g) with a yield of 22.8%.

$^1$H-NMR (CDCl$_3$) δ: 2.17 (3H, s), 2.49 (3H, s), 2.88 (1H, dd), 2.98 (1H, d), 3.31 (3H, s), 3.66 (1H, dd), 3.72 (1H, dd), 4.12 (1H, d), 4.48 (1H, dd), 4.70 (2H, br), 4.83 (1H, dd), 7.40 (2H, d), 7.82 (2H, d), 18.43 (1H, s)

IR (KBr) cm$^{-1}$; 3460, 2930, 1715, 1620, 1460, 1390, 1335, 1195, 1180

MASS 505 (C$_{22}$H$_{23}$N$_4$O$_8$S: Molecular weight 504.46)

EXAMPLE 16

Preparation of [1aS-(1aα,8β,8aα,8bα)]-8-{[(aminocarbonyl)oxy]methyl}-4,7-[(di-p-toluenesulfonyl)oxy]-1,1a,2, 8,8a,8b-hexahydro-8a-methoxy-5-methyl-6-nitroso-azirino[2',3':3,4]pyrrolo[1.2-a]indole A compound (0.27 g) prepared by the method of Example 1 is dissolved in tetrahydrofuran (40 ml). To this solution are added triethylamine (0.33 ml) and p-toluenesulfonic acid chloride (0.38 g) while cooling with ice. The mixture is stirred at a same temperature for 2.5 hours. Then the reaction solution is treated in a similar manner to that described in Example 15 to obtain the desired product (0.11 g) with a yield of 21.5%.

$^1$H-NMR (CDCl$_3$) δ: 2.18 (3H, s), 2.44 (3H, s), 2.51 (3H, s), 2.96 (1H, dd), 3.03 (1H, d), 3.23 (3H, s), 3.50 (1H, dd), 3.60 (1H, dd), 3.96 (1H, d), 4.43 (1H, dd), 4.69 (1H, dd), 4.93 (2H, br), 7.31 (2H, d), 7.40 (2H, d), 7.82 (2H, d), 7.84 (2H, d)

IR (KBr) cm$^{-1}$; 3460, 2925, 1715, 1640, 1615, 1485, 1460, 1390, 1340, 1195, 1180

MASS 659 (C$_{29}$H$_{30}$N$_4$O$_{10}$S$_2$: Molecular weight 658.59)

EXAMPLE 17

Preparation of [1aS-(1aα,8β,8aα,8bα)]-8-{[(aminocarbonyl)oxy]methyl}-6-[(benzoyl)azo-]-4,7-dihydroxy-1,1a,2,8,8a,8b-hexahydro-8a-methoxy-5-methyl-azirino-[2′,3′:3,4]pyrrolo[1,2-a]indole Mitomycin A (1.00 g) is dissolved in methanol (50 ml). With agitation is added benzoylhydrazine (1.17 g), followed by addition of potassium carbonate (0.10 g). The mixture is stirred at ambient temperature for 3 hours. The solvent is removed from the reaction solution by evaporation under reduced pressure. The residual material is subjected to silica gel chromatography using a solvent system of chloroform/methanol (6:1 v/v) to obtain the desired product as yellow-grayish powders (1.04 g) with a yield of 80.1%.

$^1$H-NMR (CDCl$_3$/d$_6$-DMSO) δ: 2.19 (3H, s), 2.83 (1H, m), 3.00 (1H, m), 3.24 (3H, s), 3.59 (1H, d), 3.63 (1H, dd), 4.32 (1H, d), 4.39 (1H, dd), 4.83 (1H, dd), 5.61 (2H, br), 7.54 (3H, m), 8.00 (2H, dd), 8.96 (1H, br), 17.04 (1H, s).

$^{13}$C-NMR (CDCl$_3$/d$_6$-DMSO) δ: 10.3, 31.7, 36.2, 42.5, 49.3, 49.8, 60.8, 105.6, 109.3, 120.8, 127.6, 128.8, 132.6, 140.7, 141.6, 156.8, 156.9, 164.4, 173.5

IR (KBr) cm$^{-1}$; 3430, 3204, 1707, 1652, 1611, 1578, 1481, 1451, 1381, 1328, 1240, 1154, 1068, 922.

MASS 454 (C$_{22}$H$_{23}$N$_5$O$_6$: Molecular weight 453.46)

EXAMPLE 18

Preparation of [1aS-(1aα,8β,8aα,8bα)]-6-[(acetyl)azo]-8-{[(aminocarbonyl)oxy]methyl}-4,7-dihydroxy-1,1a,2,8,8a,8b-hexahydro-8a-methoxy-5-methyl-azirino[2′,3′:3,4]pyrrolo[1,2-a]indole In a similar manner to that described in Example 17, mitomycin A (205 mg), acethydrazide (130 mg) and potassium carbonate (100 mg) are used to obtain the desired product (120 mg) with a yield of 52.2%.

$^1$H-NMR (d$_6$-DMSO) δ: 2.01 (3H, s), 2.24 (3H, s), 2.75 (1H, m), 2.83 (1H, d), 3.14 (3H, s), 3.49 (1H, d), 4.07 (1H, t), 4.07 (1H, d), 4.63 (1H, dd), 6.55 (2H, br), 15.37 (1H, s).

IR (KBr) cm$^{-1}$; 3450, 3182, 1699, 1618, 1552, 1484, 1378, 1327, 1193, 1167, 1061, 933

MASS 392 (C$_{17}$H$_{21}$N$_5$O$_6$: Molecular weight 391.38)

EXAMPLE 19

Preparation of 1aS-(1aα,8β,8aα,8bα)]-6-[(4″-aminobenzoyl)azo]-8-{[(a minocarbonyl)oxy]methyl}-4,7-dihydroxy-1,1a,2,8-,8a,8b-hexahydro-8a-methoxy-5-methyl-azirino[2′,3′:3,4]pyrrolo[1,2-a)indole In a similar manner to that described in Example 17, mitomycin A (302 mg), 4-aminobenzoylhydrazine (389 mg) and potassium carbonate (150 mg) are used to obtain the desired product (163 mg) with a yield of 40.5%.

$^1$H-NMR (d$_6$-DMSO) δ: 2.08 (3H, s), 2.76 (1H, dd), 2.85 (1H, d), 3.15 (3H, s), 3.50 (1H, d), 4.11 (1H, d), 4.11 (1H, dd), 4.69 (1H, dd), 6.07 (2H, s), 6.53 (1H, dd), 6.58 (2H, br), 6.66 (2H, d), 7.63 (2H, d), 16.93 (1H, s).

IR (KBr) cm$^{-1}$; 3380, 1710, 1603, 1480, 1400, 1256, 1185, 1068, 928

MASS 469 (C$_{22}$H$_{24}$N$_6$O$_6$: Molecular weight 468.46)

EXAMPLE 20

Preparation of [1aS-(1aα,8β,8aα,8bα)]-8-{[(aminocarbonyl)oxy]methyl}-4,7-dihydroxy-1,1a,2,8,8a,8b-hexahydro-6-[(4″-hydroxybenzoyl)azo]-8a-methoxy-5-methyl-azirino[2′,3′:3,4]pyrrolo[1,2-a] indole In a similar manner to that described in Example 17, mitomycin A (301 mg), 4-hydroxybenzoylhydrazine (126 mg) and potassium carbonate (107 mg) are used to obtain the desired product (222 mg) with a yield of 58.2%.

$^1$H-NMR (d$_6$DMSO) δ: 2.07 (3H, s), 2.76 (1H, d), 2.86 (1H, d), 3.15 (3H, s), 3.51 (1H, d), 4.09 (1H, dd), 4.12 (1H, d), 4.69 (1H, dd), 6.56 (2H, br), 6.95 (2H, d), 7.78 (2H, d), 17.01 (1H, s)

IR(KBr) cm$^{-1}$; 3400, 1710, 1610, 1480, 1390, 1242, 1175, 1078, 928

MASS 470 (C$_{22}$H$_{23}$N$_5$O$_7$: Molecular weight 469.45)

EXAMPLE 21

Preparation of [1aS-(1aα,8β,8aα,8bα)]-8-{[(aminocarbonyl)oxy]methyl}-6-[(benzoyl)azo]-4,7-dihydroxy-1,5-dimethyl-1,1a,2,8,8a,8b-hexahydro-8a-methoxy-azirino[2′,3′:3,4-]pyrrolo[1,2-a]indole In a similar manner to that described in Example 17, mitomycin F (200 mg), benzoylhydrazine (229 mg) and potassium carbonate (77 mg) are used to obtain the desired product (230 mg) with a yield of 89.5%.

$^1$H-NMR (CDCl$_3$/d$_6$-DMSO) δ: 2.21 (3H, s), 2.27 (1H, dd), 2.28 (3H, s), 2.40 (1H, d), 3.22 (3H, s), 3.56 (1H, dd), 3.63 (1H, dd), 4.30 (1H, dd), 4.32 (1H, d), 4.84 (1H, dd), 5.19 (2H, br), 7.53 (3H, m), 8.02 (2H, dd), 8.63 (1H, br), 17.01 (1H,s)

IR (KBr) cm$^{-1}$: 3430, 3204, 1708, 1569, 1484, 1398, 1346, 1237, 1156, 1067, 936

MASS 468 (C$_{23}$H$_{25}$N$_5$O$_6$: Molecular weight 467.49)

EXAMPLE 22

Preparation of [1aS-(1aα,8β,8aα,8bα)]-6-[(benzoyl)azo]-4,7-dihydroxy-1,5-dimethyl-1,1a,2,8,8a,8b-hexahydro-8-hydroxymethyl-8a-methoxy-azirino-[2′,3′:3,4[pyrrolo]1,2-a]indole In a similar manner to that described in Example 17, decarbamoylmitomycin F (Chemical Abstracts, 74, 99920n; 1971) (100 mg), benzoylhydrazine (129 mg) and potassium carbonate (43 mg) are used to obtain 88 mg of the desired product with a yield of 66.9%.

¹H-NMR (CDCl₃) δ: 2.17 (3H, s), 2.17 (1H, m), 2.18 (3H, s), 2.18 (1H, m), 3.18 (3H, s), 3.42 (1H, dd), 3.54 (1H, d), 4.01 (1H, m), 4.00 (1H, dd), 7.55 (3H, m), 7.99 (2H, m), 16.83 (1H, s).

IR (KBr) cm⁻¹: 3400, 2876, 1674, 1483, 1395, 1349, 1236, 1153, 1067, 943

MASS 425 ($C_{22}H_{24}N_4O_5$: Molecular weight 424.46)

EXAMPLE 23

Preparation of [1aS-(1aα,8β, 8aα,8bα)]-8-{[(aminocarbonyl)oxy]methyl}-4,7-dihydroxy-1,1a,2,8-,8a,8b-hexahydro-6[(2″-imidazolinyl)azo]-8a-methoxy-5-methyl-azirino[2′,3′:3,4]pyrrolo[1,2-a]indole In a similar manner to that described in Example 17, mitomycin A (1.01 g), 3-hydrazino-2-imidazoline hydrobromate (0.48 g) and potassium carbonate (0.25 g) are used to obtain the desired product (0.40 g) with a yield of 36.8%.

¹H-NMR (d₆-DMSO) δ: 2.08 (3H, s), 2.78 (1H, m), 2.89 (1H, m), 3.16 (3H, s), 3.55 (1H, d), 3.80 (4H, s), 4.04 (1H, dd), 4.15 (1H, d), 4.72 (1H, dd), 6.52 (2H, br), 16.51 (1H, br).

IR (KBr) cm⁻¹: 3400, 1710, 1640, 1578, 1488, 1410, 1338, 1215, 1078, 1037, 1000, 910

MASS 418 ($C_{18}H_{23}N_7O_5$: Molecular weight 417.43)

EXAMPLE 24

Preparation of [1aS-(1aα,8β,8aα,8bα)-8-{[(aminocarbonyl)oxy]methyl}4,7-dihydroxy-1,1a,2,8,8a,8b hexahydro-8a-methoxy-6-[(methoxycarbonyl)azo[-5-methyl-azirino[2′,3′:3,4]pyrrolo[1,2-a[indole Mitomycin A (300 mg) is dissolved in methanol (35 ml). Methoxycarbonylhydrazine (200 mg) is added to this solution with agitation. The mixture is stirred at ambient temperature for 24 hours. The solvent is removed from the reaction solution by evaporation under reduced pressure. The residual material is subjected to silica gel chromatography using a solvent system of chloroform/methanol (9:1 v/v) to obtain the desired product (140 mg) as reddish-orange powders with a yield of 40.0%.

¹H-NMR (d₆-DMSO) δ: 2.01 (3H, s), 2.75 (1H, m), 2.84 (1H, m), 3.14 (3H, s), 3.39 (1H, dd), 3.49 (1H, d), 3.77 (3H, s), 4.06 (1H, dd), 4.09 (1H, d), 4.64 (1H, dd), 6.52 (2H, br), 9.48 (1H, br), 15.61 (1H, s).

IR(KBr) cm⁻¹: 3400, 1708, 1620, 1490, 1455, 1392, 1338, 1240, 1176, 1065

MASS 408 ($C_{17}H_{21}N_5O_7$: Molecular weight 407.38)

EXAMPLE 25

Preparation of [1aS-(1aα,8β,8aα,8bα)]-6-[aminocarbonyl)azo]-8-{[(aminocarbonyl)oxy]methyl}-4,7-dihydroxy-1,1a,2,8-,8a,8b-hexahydro-8a-methoxy-5-methyl-azirino[2′,3′:3,4]pyrrolo[1,2-a]indole In a similar manner to that described in Example 24, mitomycin A (300 mg), semicarbazide hydrochloride (190 mg) and triethylamine (0.5 ml) are used to obtain the desired product (200 mg) with a yield of 59.3%.

¹H-NMR (d₆-DMSO) δ: 2.04 (3H, s), 2.75 (1H, m), 2.81 (1H, m), 3.14 (3H, s), 3.42 (1H, d), 3.42 (1H, dd), 4.07 (1H, d), 4.08 (1H, dd), 4.67 (1H, dd), 6.14 (2H, br), 6.95 (2H, s), 8.83 (1H, s), 14.84 (1H, s).

IR (KBr) cm⁻¹: 3450, 3196, 1705, 1616, 1556, 1487, 1411, 1340, 1199, 1170, 1061, 935

MASS 393 ($C_{16}H_{20}N_6O_6$ Molecular weight 392.37)

EXAMPLE 26

Preparation of [1aS-(1aα, 8β, 8aα,8bα)-8-{[(aminocarbonyl)oxy]methyl}-4,7-dihydroxy-1,1a,2,8-,8a,8b-hexahydro-8a-methoxy-5-methyl-6-{[(phenyl)aminocarbonyl]azo}-azirino[2′,3′:3,4]pyrrolo[1,2-a]indole Mitomycin A (300 mg) is dissolved in methanol (100 ml). To this solution is added 4-phenylsemicarbazide (210 mg) with agitation. The mixture is stirred at ambient temperature for 7 hours. The resultant precipitates are filtered The crystals are washed several times with ether to obtain the desired product coloured in reddish-orange (190 mg) with a yield of 47.6%.

¹H-NMR (d₆-DMSO) δ: 2.12 (3H, s), 2.76 (1H, m), 2.86 (1H, d), 3.16 (3H, s), 3.41 (1H, dd), 3.49 (1H, d), 3.50 (1H, dd), 4.09 (1H, d), 4.76 (1H, dd), 6.51 (2H, br), 7.04 (1H, m), 7.32 (1H, m), 7.61 (1H, m), 9.64 (1H, s), 15.53 (1H, s)

IR (KBr) cm⁻¹: 3450, 3308, 1705, 1604, 1539, 1481, 1446, 1329, 1153, 1059, 933

MASS 469 ($C_{22}H_{24}N_6O_6$: Molecular weight 468.47)

EXAMPLE 27

Preparation of 1aS-(1aα,8β, 8aα, 8bα)]-8-{[(aminocarbonyl)oxy]methyl}-6-[(benzoyl)azo]-4,8a-dimethoxy-1,1α,2,8,8a,8b-hexahydro-7-hydroxy-5-methyl-azirino[2′,3′:3,4]pyrrolo[1,2-a]indole A compound (1.09 g) prepared by the method of Example 17 is dissolved in DMF (100 ml). To this solution is added sodium methoxide (0.14 g). The mixture is stirred at ambient temperature for 30 minutes. To the solution is added further methyl iodide (0.22 ml). The solution is stirred at ambient temperature for 2.5 hours. The solvent is removed from the reaction solution by evaporation under reduced pressure. To the resultant oily material are added chloroform and water. The extracted chlorform layer is dried by using anhydrous sodium sulfate, followed by removal of chloroform by evaporation under reduced pressure. The residual material is subjected to silica gel chromatography using a solvent system of chloroform/acetone (1:1 v/v) to obtain an oily material which is purified by thin layer silica gel chromatography using a solvent system of chloroform/acetone (1:2 v/v) to yield the desired product as yellowish brown powders (0 14 g; yield 13.1%).

¹H-NMR (CDCl₃) δ: 2.28 (3H, s), 2.88 (1H, m), 2.99 (1H, d), 3.26 (3H, s), 3.57 (1H, d), 3.73 (3H, s), 3.75 (1H, dd), 4.22 (1H, d), 4.57 (1H, dd), 4.84 (2H, br), 4.92 (1H, s), 7.55 (3H, m), 8.05 (2H, m), 17.08 (1H, s).

IR (KBr) cm⁻¹: 3430, 1696, 1608, 1573, 1480, 1452, 1380, 1320, 1239, 1065, 982

MASS 468 ($C_{23}H_{25}N_5O_6$: Molecular weight 467.49)

EXAMPLE 28

Preparation of [1aS-(1aα,8β,8aα,8bα)]-8-{[(aminocarbonyl)oxy]methyl}-4,7-dihydroxy-1,1a,2,8,8a,8b-hexahydro-6-[(2″-hydroxybenzoyl)azo]-8a-methoxy-5-methyl-azirino[2′,3′:3,4]pyrrolo[1,2-a]indole In a similar manner to that described in Example 17, mitomycin A (215 mg), salicylhydrazide (90 mg) and potassium carbonate (100 mg) are treated to obtain the desired product (148 mg) with a yield of 53.6%.

$^1$H-NMR (CDCl$_3$) δ: 2.08 (3H, s), 2.77 (1H, d), 2.86 (1H, d), 3.16 (3H, s), 3.50 (1H, d), 4.10 (1H, d), 4.10 (1H, dd), 4.71 (1H, dd), 6.54 (2H, br), 6.97 (2H, m), 7.44 (1H, m), 7.85 (1H, m), 16.52 (1H,, s).

IR (KBr) cm$^{-1}$: 3400, 1710, 1648, 1485, 1405, 1340, 1240, 1160, 1072, 928

MASS 470 (C$_{22}$H$_{23}$N$_5$O$_7$: Molecular weight 469.45)

EXAMPLE 29

Preparation of [1aS-(1aα,8α,8aα,8bα)]-8-{[(aminocarbonyl)oxy]methyl}-6-[(benzoyl)azo]-1,5-dimethyl-1,1a,2,8,8a,8b-hexahydro-4,7,8a-trihydroxy-azirino[2',3':3,4]pyrrolo[1,2-a]indole In a similar manner to that described in Example 17, mitomycin B (1.25 g), benzoylhydrazine (1.21 g) and potassium carbonate (0.30 g) are used to obtain the desired product (0.90 g) with a yield of 69.6%.

$^1$H-NMR (d$_6$-DMSO) δ: 2.06 (3H, s), 2.21 (3H, s), 2.29 (1H, d), 2.47 (1H, d), 3.50 (1H, dd), 3.57 (1H, d), 4.04 (1H, d), 4.14 (1H, dd), 4.78 (1H, dd), 6.42 (2H, br), 6.44 (1H, s), 7.62 (3H, m) 7.90 (2H, dd), 9.80 (1H, s), 17.23 (1H, s)

IR (KBr) cm$^{-1}$: 3440, 3198, 1704, 1662, 1616, 1576, 1488, 1455, 1354, 1239, 1167, 1068

MASS 454 (C$_{22}$H$_{23}$N$_5$O$_6$: Molecular weight 453.46)

EXAMPLE 30

Preparation of [1aS-(1aα,8β,8aα,8bα)]-8-{[(aminocarbonyl)oxy]methyl}-4,7-dihydroxy-1,1a,2,8,8a,8b-hexahydro-6-[(tert-butoxycarbonyl)azo]-8a-methoxy-5-methyl-azirino[2',3':3,4]pyrrolo[1,2-a]indole In a similar manner to that described in Example 17, mitomycin A (250 mg), tert-butoxycarbonylhydrazine (284 mg) and potassium carbonate (150 mg) are treated to obtain the desired product (138 mg) with a yield of 42.7%.

$^1$H-NMR (d$_6$-DMSO) δ: 1.48 (9H, s), 2.00 (3H, s), 2.75 (1H, m), 2.84 (1H, m), 3.14 (3H,s), 3.35 (1H, dd), 3.48 (1H, d), 4.07 (1H, d), 4.08 (1H, dd), 4.65 (1H, dd), 6.50 (2H, br), 9.36 (1H, br), 15.41 (1H, s)

IR (KBr) cm$^{-1}$: 3446, 3312, 1723, 1698, 1615, 1557, 1532, 1481, 1375, 1213, 1162, 1056, 1033, 934

MASS 450 (C$_{20}$H$_{27}$N$_5$O$_7$: Molecular weight 449.46)

EXAMPLE 31

Preparation of [1aS-(1aα,8β,8aα,8bα)-8-{[(aminocarbonyl)oxy]methyl]-4,7-dihydroxy-1,1a,2,8,8a,8b-hexahydro-8a-methoxy-5-methyl-6-{[(methylthio)thiocarbonyl]azo}-azirino[2',3';3,4]pyrrolo[1,2-a]indole In a similar manner to that described in Example 17, mitomycin A (300 mg), [(methylthio)thiocarbanyl]hydrazine (320 mg) and potassium carbonate (145 mg) are treated to obtain the desired product (267 mg) with a yield of 70.7%.

$^1$H-NMR (d$_6$-DMSO) δ: 2.04 (3H, s), 2.57 (3H, s), 2.77 (1H, m), 2.84 (1H, m), 3.16 (3H, s), 3.40 (1H, dd), 3.53 (1H, d), 4.09 (1H, dd), 4.11 (1H, d), 4.64 (1H, dd), 6.54 (2H, br), 10.00 (1H, s), 16.95 (1H, s)

IR (KBr) cm$^{-1}$: 3280, 2930, 1707, 1610, 1578, 1485, 1395, 1315, 1250, 1134, 1065, 932

MASS 440 (C$_{17}$H$_{21}$N$_5$O$_5$S : Molecular weight 439.51)

EXAMPLE 32

Preparation of [1aS-(1aα,8β,8aα,8bα)-8-{[(aminocarbonyl)oxy]methyl}-6-[(aminothiocarbonyl)azo]-4,7-dihydroxy-1,1a,2,8,8a,8b-hexahydro-8a-methoxy-5-methyl-azirino[2',3':3,4]pyrrolo[1,2-a]indole In a similar manner to that described in Example 24, mitomycin A (0.30 g) and thiosemicarbazide (0.39 g) are treated to obtain the desired product (80 mg; yield 22.8%).

$^1$H-NMR (d$_6$-DMSO) δ: 2.05 (3H, s), 2.76 (1H, m), 2.86 (1H, m), 3.16 (3H, s), 3.41 (1H, dd), 3.48 (1H, d), 4.09 (1H, d), 4.10 (1H, dd), 4.67 (1H, dd), 6.46 (2H, br), 8.93 (1H, s), 15.60 (1H, s)

IR (KBr) cm$^{-1}$: 3410, 1707, 1600, 1570, 1453, 1379, 1328, 1213, 1153, 1060, 925

MASS 409 (C$_{16}$H$_{20}$N$_6$O$_3$S : Molecular weight 408.44)

EXAMPLE 33

Preparation of [1aS-(1aα,8α,8aα,8bα)-8-{[(aminocarbonyl)oxy]-methyl-}6-[(benzoyl)azo]-7,8a-dihydroxy-1,5-dimethyl-1,1a,2,8,8a,8b-hexahydro-4-methoxy-azirino[2',3':3,4-]pyrrolo[1,2-a]indole In a similar manner to that described in Example 27, a compound prepared by the method of Example 29 (553 mg), sodium methoxide (72 mg) and methyl iodide (0.15 ml) are treated to obtain the desired product (80 mg) with a yield of 14.0%.

$^1$H-NMR (d$_6$-DMSO) δ: 2.11 (3H, s), 2.21 (3H, s), 2.32 (1H, m), 3.51 (1H, dd), 3.61 (1H, d), 3.69 (3H, s), 3.90 (1H, d), 4.16 (1H, dd), 4.78 (1H, dd), 6.53 (1H, s), 6.45 (2H, br), 7.66 (3H, m), 7.92 (2H, m), 17.38 (1H, s),

IR (KBr) cm$^{-1}$: 3410, 1729, 1691, 1616, 1506, 1487, 1452, 1387, 1322, 1232, 1170, 1061, 960

MASS 468 (C$_{23}$H$_{25}$N$_5$O$_6$: Molecular weight 467.49)

EXAMPLE 34

Preparation of [1aS-(1aα,8β,8aα,8bα)-4-acetyloxy-8-{[(aminocarbonyl)oxy]methyl}-1,1a,2,8,8a,8b-hexahydro-7-hydroxy-8a-methoxy-5-methyl-6-nitroso-azirino[2',3':3,4]pyrrolo[1,2-a]indole A compound prepared by the method of Example 11 (0.66 g) is dissolved in methanol (30 ml). The solution is added to an aqueous solution of 15% hydroxylamine (0.31 ml). The mixture is stirred at ambient temperature for one hour. After further addition of an aqueous solution of 15% hydroxylamine (0.31 ml), the solution is stirred at ambient temperature for 40 minutes. The solvent is removed from the solution by evaporation under reduced pressure. The resultant oily material is subjected to silica gel chromatography using a solvent system of chloroform/methanol (15:1 v/v) to obtain the desired product (0.08 g) with a yield of 14.3%.

$^1$H-NMR (CDCl$_3$) δ: 2.27 (3H, s), 2.37 (3H, s), 2.86 (1H, dd), 2.98 (1H, d), 3.18 (3H, s), 3.43 (1H, dd), 3.70 (1H, dd), 3.92 (1H, d), 4.50 (1H, dd), 4.80 (1H, dd), 4.95 (2H, br), 18.66 (1H, s)

IR (KBr) cm$^{-1}$: 3400, 2950, 1710, 1620, 1480, 1340, 1210, 1190, 1070

MASS 393 (C$_{17}$H$_{20}$N$_4$O$_7$: Molecular weight 392.38)

EXAMPLE 35

Preparation of
[1aS-(1aα,8β,8aα,8bα)]-8-{[(aminocarbonyl)oxy]-methyl}-4-ethoxy-1,1a,2,8,8,8a,8b-hexahydro-7-hydroxy-8a-methoxy-5-methyl-6-nitroso-azirino[2',3':3,4]pyrrolo[1,2-a]indole A compound prepared by the method of Example 1 (0.50 g), tert-butoxy potassium (0.17 g) and ethyl iodide (0.17 ml) are treated in a similar manner to that described in Example 6 to obtain the desired product (0.14 g; yield 25.8%).

$^1$H-NMR (CDCl$_3$): 1.41 (3H, t), 2.28 (3H, s), 2.87 (1H, m), 2.98 (1H, m), 3.23 (3H, s), 3.52 (1H, d), 3.69 (1H, dd), 3.89 (2H, m), 4.28 (1H, d), 4.52 (1H, t), 4.82 (2H, br), 4.85 (1H, dd), 19.05 (1H, s)

IR(KBr) cm$^{-1}$: 3450, 2930, 1709, 1600, 1480, 1338, 1220, 1068

MASS 379 (C$_{17}$H$_{22}$N$_4$O$_6$: Molecular weight 378.38)

FORMULATION 1

Injectable solution:

A compound prepared by the method of Example 1 (10 mg) is put into a brown vial (10 ml) under sterile conditions to obtain a sterile powder. Prior to use, 50% aqueous ethanol (5 ml) is added to the powder under sterile conditions with vigorous stirring.

FORMULATION 2

Tablet:

A compound prepared by the method of Example 6 (20 mg), lactose (170 mg), potato starch (20 mg), hydroxypropylcellulose (4 mg) and magnesium stearate (1 mg) were admixed and pressed to form a tablet in conventional manner.

FORMULATION 3

Suppository:

A compound prepared by the method of Example 8 (20 mg), Witepsol H-15 (750 mg) and Witepsol E-15 (320 mg) are used to form a suppository in conventional manner. "Witepsol" is a Trade Mark for suppository bases commercially available from Diamond Nobel AG., West Germany.

The following Experiments illustrate the pharmacological effects of typical Compounds (I).

EXPERIMENT 1

Table 3 indicates the effects of typical Compounds (I) against Hela S$_3$ culture cells. In this table, IC$_{50}$ denotes the concentration of the test compound capable of reducing the number of cells to 50% the number of untreated cells.

TABLE 3

| \multicolumn{4}{c}{Effects upon Hela S$_3$ cultured cells} |
|---|---|---|---|
| Compound (Example No.) | IC$_{50}$ (μg/ml) | Compound (Example No.) | IC$_{50}$ (μg/ml) |
| 1 | 1.135 | 18 | 0.54 |
| 6 | 0.005 | 21 | 0.75 |
| 7 | 0.013 | 22 | 0.131 |
| 8 | 0.200 | 23 | 0.162 |
| 9 | 0.005 | 24 | 0.012 |
| 10 | 0.004 | 25 | 0.003 |
| 11 | 0.020 | 28 | 0.08 |
| 15 | 0.027 | mitomycin-C | 0.004 |
| 17 | 14.9 | | |

The experiment was carried out in the following manner:

Cultured cells of Hela S$_3$ were added to a MEM medium containing 10% (V/V) of bovine fetal serum and 292 mg/ml of glutamine to obtain a cell suspension of 3 × 10$^4$ cells/ml. The cell suspension was poured into each well (1 ml/well) of a 24 well-multiplate for culturing at 37° C. in an incubator containing carbon dioxide (5%) and air (95%). After 24 hours, samples were dissolved or suspended in PBS, ethanol or dimethylsulfoxide and added to the medium at different concentrations, followed by culturing at 37° C. for 72 hours in the same incubator. An aspirator was used to collect the medium from each well. The surface of each medium was washed by adding PBS (1 ml) gently, and then PBS was sucked out. PBS containing trypsin (0.05%) and EDTA (0.02%) was poured into each well. After pipetting, the number of cells in each suspension was counted by the use of a microcell counter (commercial product of Toa Iyo Denshi K.K., Japan). By reference to a curve showing the concentration vs. the number of cells, the IC$_{50}$ (concentration of sample capable of reducing the number of cells to 50% of the number of control untreated cells) was measured.

EXPERIMENT 2

Table 4 indicates the effects of typical Compounds (I) upon Sarcoma 180 solid tumour. In this table, C.I. denotes chemotherapeutic index, calculated as C.I.=(LD$_{50}$)/(ED$_{50}$), wherein LD$_{50}$ denotes the value of acute toxicity, and ED$_{50}$ denotes the dose of a sample which is capable of reducing the volume of Sarcoma 180 solid tumour to 50% of the corresponding volume of the solid tumour of untreated group. In this table, the value of (WBC$_{4000}$)/(ED$_{50}$) indicates the ratio of the dose capable of reducing the number of peripheral leucocytes to 4000 to ED$_{50}$, which suggests the influence upon the number of peripheral leucocytes.

TABLE 4

| \multicolumn{4}{c}{Effects upon Sarcoma 180 solid tumour} |
|---|---|---|---|
| Compound (Example No.) | LD$_{50}$ (mg/kg) | C.I. | $\frac{WBC_{4000}}{ED_{50}}$ |
| 1 | 53 | 2.0 | 0.7 |
| 4 | 100 | 2.8 | >1.4 |
| 6 | 75 | 5.6 | 2.7 |
| 8 | 100 | 2.1 | 1.1 |
| 10 | >100 | >0.56 | >0.56 |
| 11 | 38 | 2.0 | 0.9 |
| 13 | >100 | >0.74 | >0.74 |
| 15 | 56 | 2.6 | 3.9 |
| 21 | >100 | >1.0 | 0.62 |
| 23 | >100 | >0.6 | 0.5 |
| 24 | >100 | >0.3 | 0.6 |
| 31 | 50 | 2.5 | 1.1 |
| mitomycin C | 8.4 | 1.9–2.8 | 0.7–1.1 |

LD$_{50}$, ED$_{50}$ and WBC$_{4000}$ were calculated respectively as follows:

(1) LD$_{50}$

The test compound was abdominally administered once to ddy mice, each group consisting of 5 animals. After this, the death ratio of the animals of the test group was observed for 14 days, from which LD$_{50}$ was calculated by Behrens-Körber's method.

(2) ED$_{50}$

5 × 10$^6$ cells of Sarcoma 180 solid tumour were abdominally implanted into a ddy mouse. 7 days after this, the cells were collected from the ascites fluid. The cells were washed once with physiological saline under sterile conditions and suspended in physiological saline to obtain a cell suspension containing $5 \times 10^7$ cells/ml of which 0.1 ml was implanted into a ddy male mouse (body weight $20 \pm 2$ g) under the skin of the right armpit. The test compound was dissolved in physiological saline or the same solution containing Tween 80. 24 hours after implantation of the tumour cells, 0.1-0.2 ml of the solution containing the test compound was administered to the tail vein of each animal in the test group consisting of 5 animals. 7 days after the implantation, the major axis (a) and minor axis (b) of the tumour were measured to calculate the volume of the tumour as "a"$\times$"$b^2$"/2. The antitumour effect was indicated by T/C which is the ratio of the tumour volume in the test animals to the corresponding volume of the control (untreated) animals.

T/C ratios and the dose were respectively plotted on the ordinate using an arithmetic scale and on the abscissa using a logarithmic scale, the relationship between the dosage and the T/C ratio being converted to a straight line by the least squares method. From the straight tropic line thus-obtained, the dosage corresponding to a T/C=0.5 viz. $ED_{50}$ was determined.

(3) $WBC_{4000}$

Sarcoma 180 solid tumour cells ($5 \times 10^6$) were subcutaneously implanted under the skin of the right armpit of each mouse (body weight $20 \pm 2$ g) of a group consisting of 5 male mice (ddy strain). 24 hours after this, a test compound was intraperitoneally administered to each animal. 4 days later, blood (0.02 ml) was collected from the suborbital plexus vein of each tumour-carrying animal. The collected sample of blood was dispersed in 9.98 ml of Cellkit Seven solution. One drop of saponin solution was added to the sample to dissolve erythrocytes and then a microcell counter was used to measure the number of leucocytes. On graph paper, the number of leucocytes was plotted on the ordinate using an arithmetic scale, and the dosage was plotted on the abscissa using a logarithmic scale to show the relationship of the dosage to the number of peripheral leucocytes, from which the value of $WBC_{4000}$ viz. a value capable of giving 4000 peripheral leucocytes per $mm^3$ (about half of the corresponding value in normal mice) was obtained.

We claim:

1. Mitomycin compounds represented by the formula:

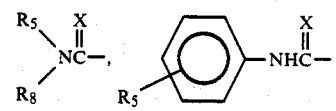

wherein A is ON— or $R_4N=N—$ wherein $R_4$ is selected from

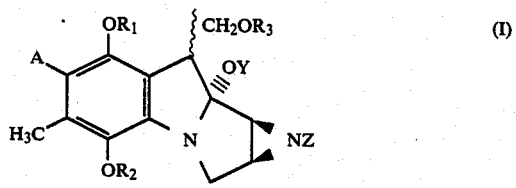

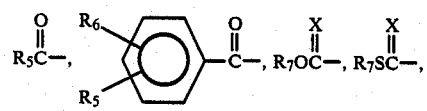

(wherein
$R_5$ and $R_8$ are each independently selected from hydrogen, alkyl having 1-6 carbon atoms and cycloalkyl having 3-6 carbon atoms;
$R_6$ is selected from hydrogen, halogen, hydroxy, alkoxy having 1-6 carbon atoms, amino and nitro;
$R_7$ is selected from alkyl having 1-6 carbon atoms and cycloalkyl having 3-6 carbon atoms;
and X is selected from oxygen, sulphur and imino) and an unsubstituted or substituted heterocyclic group selected from imidazolyl, imidazolinyl, thiazolyl, thiazolinyl, oxazolyl, oxazolinyl, triazolinyl and pyrimidyl (wherein the substituent is selected from alkyl having 1-6 carbon atoms);
$R_1$ and $R_2$ are each independently selected from hydrogen, alkyl having 1-6 carbon atoms, cycloalkyl having 3-6 carbon atoms, unsubstituted or substituted phenethyl, diphenylmethyl, trityl, benzyl, phenyl and naphthyl (wherein the substituent is selected from one or two members selected from halogen, nitro, cyano, alkyl having 1-6 carbon atoms and alkoxy having 1-6 carbon atoms), unsubstituted or substituted alkanoyl having 1-6 carbon atoms and alkanesulfonyl having 1-6 carbon atoms (wherein the substituent is selected from 1, 2 or 3 halogen benzenesulfonyl, p-toluenesulfonyl and benzylsulfonyl;
$R_3$ is hydrogen or carbamoyl;
Y is hydrogen or methyl;
Z is selected from hydrogen, methyl and acetyl;
and ∼ is an α or β bond.

2. Mitomycin compounds according to claim 1 wherein one or more of $R_5$, $R_7$, $R_8$, $R_1$ and $R_2$ independently represents straight or branched alkyl of 1-6 carbon atoms or cycloalkyl of 3-6 carbon atoms.

3. Mitomycin compounds according to claim 1 wherein $R_6$ represents straight or branched alkoxy of 1-6 carbon atoms.

4. Mitomycin compounds according to claim 1 wherein $R_4$ represents imidazolyl, imidazolinyl, thiazolyl, thiazolinyl, oxazolyl, oxazolinyl, triazolinyl, or pyrimidyl optionally substituted by straight or branched alkyl of 1-6 carbon atoms.

5. Mitomycin compounds according to claim 1 wherein one or both of $R_1$ and $R_2$ independently represent phenethyl, diphenylmethyl, trityl, benzyl, phenyl or naphthyl optionally substituted by 1 or 2 groups each independently selected from halogen, nitro, cyano and straight or branched alkyl or alkoxy of 1-6 carbon atoms.

6. Mitomycin compounds according to claim 1 wherein one or both of $R_1$ and $R_2$ independently represent straight or branched alkanoyl or alkanesulfonyl of 1-6 carbon atoms optionally substituted with halogen.

7. Mitomycin compounds according to claim 1 wherein one or both of $R_1$ and $R_2$ independently represent trichloroacetyl, trifluoroacetyl, methanesulfonyl, ethanesulfonyl, isopropanesulfonyl, n-butanesulfonyl, n-hexanesulfonyl, trichloromethanesulfonyl, trifluoromethanesulfonyl, benzenesulfonyl, p-toluenesulfonyl or benzylsulfonyl.

8. (1aS-(1aα,8β,8aα,8bα))-4,7-dihydroxy-1,1a,2,8,8a,8b-hexahydro-8-hydroxymethyl-8a-methoxy-5-methyl-6-nitroso-azirino[2',3':3,4]pyrrolo[1,2-a]indole.

9. (1aS-(1aα,8β,8aα,8bα))-8-{[(aminocarbonyl)oxy]methyl}-4,8a-dimethoxy-1,1a,2,8,8a,8b-hexahydro-7-hydroxy-5-methyl-6-nitroso-azirino[2',3':3,4]pyrrolo[1,2-a]indole.

10. (1aS-(1aα,8β,8aα,8bα))-8-{[(aminocarbonyl)oxy]methyl}-1,1a,2,8,8a,8b-hexahydro-5-methyl-6-nitroso-4,7,8a-trimethoxy-azirino[2',3':3,4]pyrrolo[1,2-a]indole.

11. (1aS-(1aα,8β,8aα,8bα))-1-acetyl-4-acetyloxy-8-{[(aminocarbonyl)oxy]methyl}-1,1a,2,8,8a,8b-hexahydro-7-hydroxy-8a-methoxy-5-methyl-6-nitroso-azirino(2',3':3,4)pyrrolo(1,2-a)indole.

12. (1aS-(1aα,8β,8aα,8bα))-8-{(aminocarbonyl)oxy)methyl}-1,1a,2,8-8a,8b-hexahydro-7-hydroxy-8a-methoxy-5-methyl-6-nitroso-4-(p-toluenesulfonyl)oxy)azirino(2',3':3,4)pyrrolo(1,2-a)indole.

13. (1aS-(1aα,8β,8aα,8bα))-8-{(aminocarbonyl)oxy)methyl}-4,7-dihydroxy-1,1a,2,8,8a,8b-hexahydro-8a-methoxy-5-methyl-6-{((methylthio)thiocarbonyl)azo}azirino(2',3':3,4)pyrrolo(1,2-a)indole.

14. An antileukemia composition comprising a pharmacologically effective amount of a mitomycin compound as claimed in claim 1 in association with at least one pharmaceutically acceptable carrier and/or excipient.

15. A process for treating leukemia in a mammal comprising administering a pharmacologically effective amount of a mitomycin compound as claimed in claim 1 to said mammal.

* * * * *